US006657043B1

United States Patent
Guerret et al.

(10) Patent No.: US 6,657,043 B1
(45) Date of Patent: Dec. 2, 2003

(54) POLYALCOXYAMINES OBTAINED FROM β-SUBSTITUTED NITROXIDES

(75) Inventors: Olivier Guerret, Marcy I'Etoile (FR); Jean-Luc Couturier, Lyons (FR); Jean-Francois Lutz, Montpellier (FR); Christophe Le Mercier, Calvire et Cuire (FR); Sophie Robin, Talence (FR); Bruno Vuillemin, Billere (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/979,124
(22) PCT Filed: May 12, 2000
(86) PCT No.: PCT/FR00/01287
§ 371 (c)(1), (2), (4) Date: Mar. 15, 2002
(87) PCT Pub. No.: WO00/71501
PCT Pub. Date: Nov. 30, 2000

(30) Foreign Application Priority Data
May 19, 1999 (FR) .............................. 99 06329

(51) Int. Cl.$^7$ .............................................. C08G 73/00
(52) U.S. Cl. .................. 528/422; 528/425; 528/398; 525/333.8
(58) Field of Search ................... 528/422, 425, 528/398; 525/333.8

(56) References Cited

U.S. PATENT DOCUMENTS 5,919,871 A  7/1999  Nicol et al.

FOREIGN PATENT DOCUMENTS

WO  96 24620 WO  11/1996
WO  99 03894 WO  1/1999

OTHER PUBLICATIONS

Hammouch S O et al: "Living Diradical Polymerization" Macromolecular: Rapid, Communications, De, Wiley Vch, Weinheim, vol. 17, No. 2, Feb. 1996, pp. 149–154, XP000598224, ISSN: 1022–1336—the whole document.

Hammouch S O et al.: "Living Radical Polymerization Of Styrene In The Presence Of A Nitroxide Compound", Macromolecular: Rapid, Communications, De, Wiley Vch, Weihheim, vol. 17, No. 10, Oct. 1996, pp. 683–691, XP 000634604, ISSN: 1022–1336—the whole document.

*Primary Examiner*—Duc Truong
(74) *Attorney, Agent, or Firm*—Millen, White, Zelano, Branigan

(57) ABSTRACT

The invention relates to polyalcoxyamines obtained from beta-substituted nitroxides of formula (1) wherein A represents a di- or polyvalent structure, R1 represents a molar mass of more than 15 and is a monovalent radical, and n>2. The inventive compounds can be used as initiators for (co)polymerizations of at least one radically polymerizable monomer.

46 Claims, 5 Drawing Sheets

POLYALCOXYAMINES OBTAINED FROM β-SUBSTITUTED NITROXIDES

Figure 1:
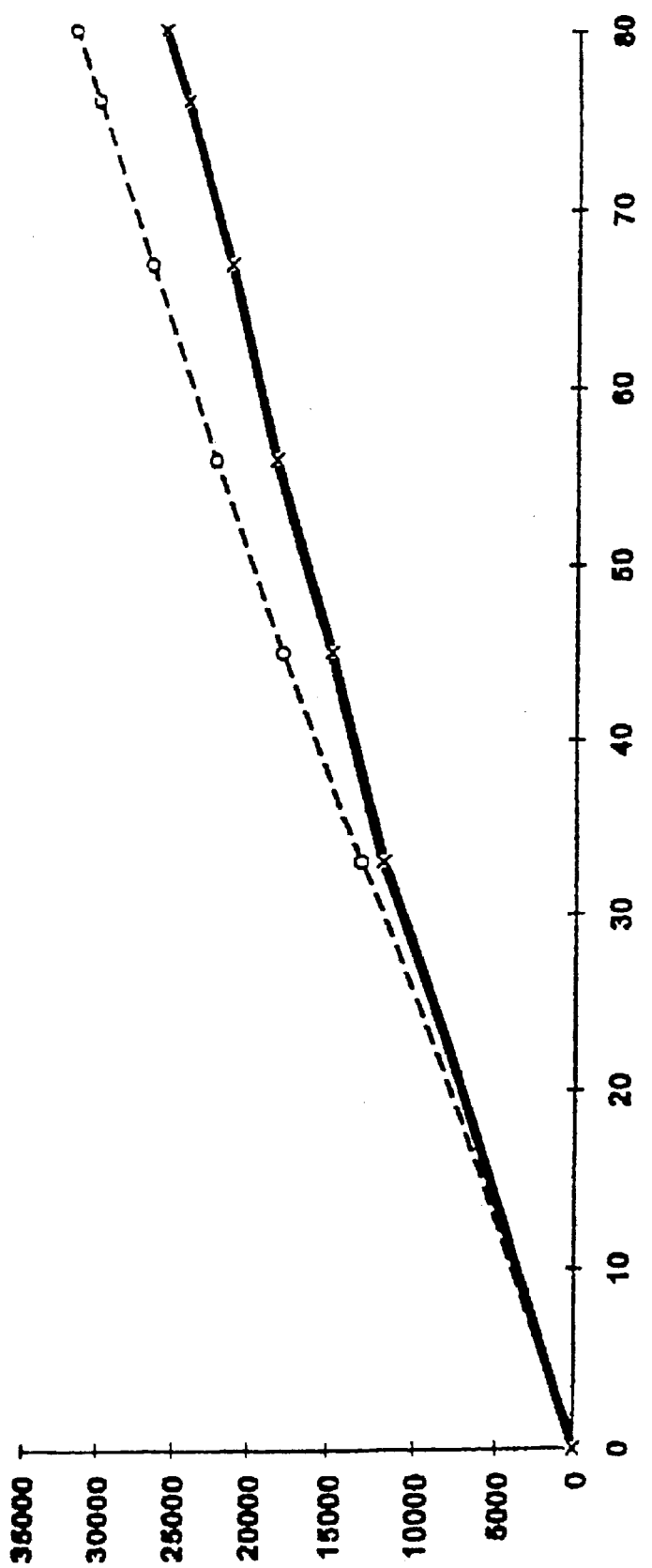

The present invention relates to polyalkoxyamines obtained from β-substituted nitroxides, which may be used especially as free-radical polymerization initiators.

Recent developments in controlled free-radical polymerization have revealed the value of polyalkoxyamines as described in Accounts of Chemical Research, 1997, 30, pages 373–382.

These polyalkoxyamines, under the action of heat, in the presence of an olefin which may undergo free-radical polymerization, initiate the polymerization while at the same time allowing it to be controlled.

The mechanism for this control may be represented diagrammatically as below:

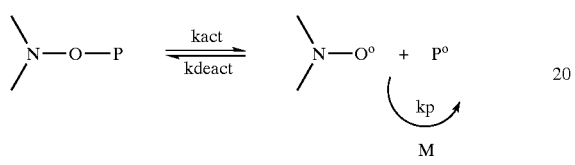

with M representing a polymerizable olefin and P representing the growing polymer chain.

The key to the control is associated with the constants $K_{deact}$, $k_{act}$ and $k_p$ (T. Fukuda and A. Goto, Macromolécules 1999, 32, pages 618 to 623). If the ratio $k_{deact}/k_{act}$ is too high, the polymerization is blocked, whereas when the ratio $k_p/k_{deact}$ is too high, when the ratio $k_{deac}/k_{act}$ is too low though, the polymerization is uncontrolled.

It has been found (P. Tordo et al., Polym. Prep. 1997, 38, pages 729 and 730; and C. J. Hawker et al., Polym. mater. Sci. Eng., 1999, 80, pages 90 and 91) that β-substituted alkoxyamines make it possible to initiate and control efficiently the polymerization of several types of monomers, whereas TEMPO-based alkoxyamines [such as (2',2',6',6'-tetramethyl-1'-piperidyloxy-)methylbenzene mentioned in Macromolecules 1996, 29, pages 5245–5254] control only the polymerizations of styrene derivatives.

The Applicant has now found that, starting with polyoxyamines of the general formula (I):

in which n≧2,

A represents a polyfunctional core and $R_L$ represents a radical with a molar mass of greater than 15, A and $R_L$ will be defined more fully later, it can synthesize polymers and copolymers with well defined architecture.

Starting with a dialkoxyamine of formula. (I) in which n=2, it is possible to synthesize triblock copolymers, each block being derived from monomers as different as alkyl acrylates and/or styrene derivatives, with excellent control of the polymerization and the polydispersity and with very short polymerization reaction times.

Thus, for example, it is possible to polymerize successively 2 monomers M1 and M2:

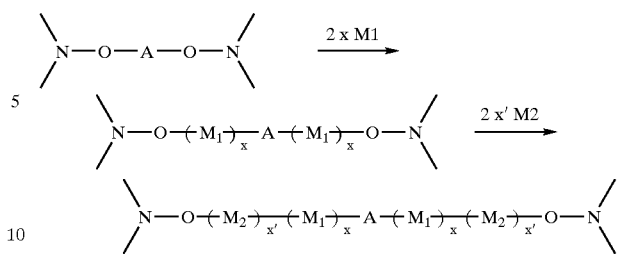

By way of example, M1=alkyl acrylate and M2=styrene.

Starting from a trialkoxyamine, "star-shaped" polymers will be obtained.

One subject of the invention is thus polyalkoxyamines of general formula (I):

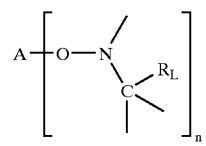

in which: n≧2,

A represents a divalent or polyvalent structure which may be chosen from the structures given below in a non-limiting manner:

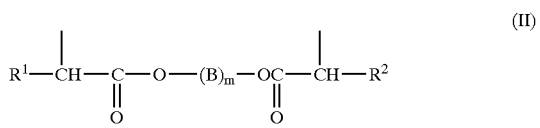

(II)

in which $R^1$ and $R^2$, which may be identical or different, represent a linear or branched alkyl radical containing a number of carbon atoms ranging from 1 to 10, phenyl or thienyl radicals optionally substituted with a halogen atom such as F, Cl or Br, or a linear or branched alkyl radical containing a number of carbon atoms ranging from 1 to 4, or alternatively with nitro, alkoxy, aryloxy, carbonyl or carboxyl radicals; a benzyl radical, a cycloalkyl radical containing a number of carbon atoms ranging from 3 to 12, a radical comprising one or more unsaturations; B represents a linear or branched alkylene radical containing a number of carbon atoms ranging from 1 to 20; m is an integer ranging from 1 to 10;

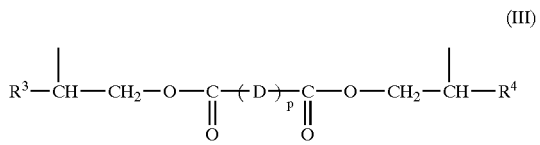

(III)

in which $R^3$ and $R^4$, which may be identical or different, represent aryl, pyridyl, furyl or thienyl radicals optionally substituted with a halogen atom such as F, Cl or Br, or with a linear or branched alkyl radical containing a number of carbon atoms ranging from 1 to 4, or alternatively with nitro, alkoxy, aryloxy, carbonyl or carboxyl radicals; D represents a linear or branched alkylene radical containing a number of carbon atoms ranging from 1 to 6, a phenylene radical or a cycloalkylene radical; p ranging from 0 to 10;

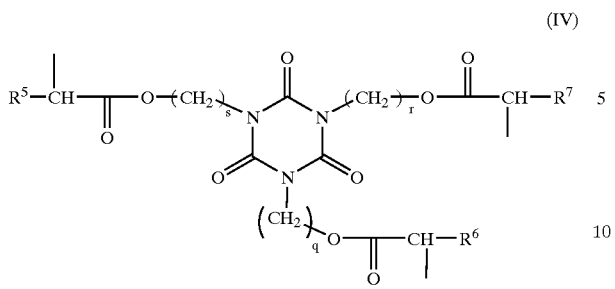
(IV)

in which $R^5$, $R^6$ and $R^7$, which may be identical or different, have the same meanings as $R^1$ and $R^2$ of formula (II), q, r and s are integers ranging from 1 to 5;

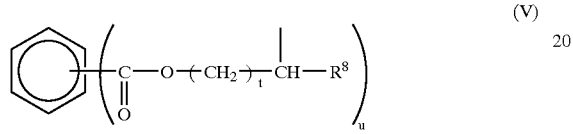
(V)

in which $R^8$ has the same meaning as $R^3$ and $R^4$ of formula (III), t is an integer ranging from 1 to 4, u is $\geq 2$ and $\leq 6$;

(VI)

in which $R^9$ has the same meaning as the radical $R^8$ of formula (V) and v is $\geq 2$ and $\leq 6$;

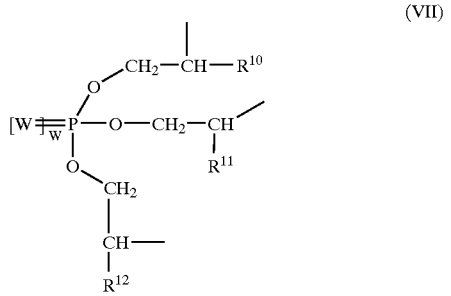
(VII)

in which $R^{10}$, $R^{11}$ and $R^{12}$, which may be identical or different, represent a phenyl radical, optionally substituted with a halogen atom such as Cl or Br, or with a linear or branched alkyl radical containing a number of carbon atoms ranging from 1 to 10; W represents an oxygen, sulfur or selenium atom, and w is equal to zero or 1;

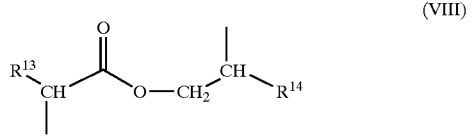
(VIII)

in which $R^{13}$ has the same meaning as $R^1$ of formula (II), and $R^{14}$ has the same meaning as $R^3$ or $R^4$ of formula (III);

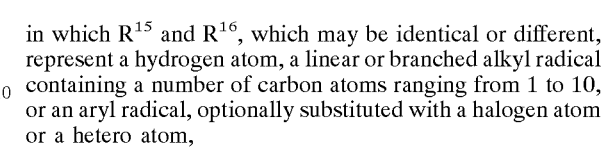
(IX)

in which $R^{15}$ and $R^{16}$, which may be identical or different, represent a hydrogen atom, a linear or branched alkyl radical containing a number of carbon atoms ranging from 1 to 10, or an aryl radical, optionally substituted with a halogen atom or a hetero atom, $R_L$ has a molar mass of greater than 15; the monovalent radical $R_L$ is said to be in a β position relative to the nitrogen atom, the remaining valencies on the carbon atom and on the nitrogen atom in formula (1) may be linked to various radicals such as a hydrogen atom, a hydrocarbon-based radical, for instance an alkyl, aryl or aralkyl radical containing from 1 to 10 carbon atoms, the carbon atom and the nitrogen atom in formula (1) may also be linked together via a divalent radical so as to form a ring; preferably, however, the remaining valencies on the carbon atom and on the nitrogen atom of formula (I) are linked to monovalent radicals; preferably, the radical $R_L$ has a molar mass of greater than 30, the radical $R_L$ may have, for example, a molar mass of between 40 and 450; by way of example, the radical $R_L$ may be a radical comprising a phosphoryl group, said radical $R_L$ preferably being represented by the formula:

(X)

in which $R^{17}$ and $R^{18}$, which may be identical or different, may be chosen from alkyl, cycloalkyl, alkoxy, aryloxy, aryl, aralkyloxy, perfluoroalkyl and aralkyl radicals and may contain from 1 to 20 carbon atoms; $R^{17}$ and/or $R^{18}$ may also be a halogen atom, for instance a chlorine or bromine or fluorine or iodine atom; the radical $R_L$ may also comprise at least one aromatic ring such as the phenyl radical or naphthyl radical, said radical possibly being substituted, for example with an alkyl radical containing from 1 to 10 carbon atoms.

According to the present invention, the monovalent radicals linked to the carbon atom bearing the radical $R_L$, which may be identical or different, may be a hydrogen atom, a linear or branched alkyl radical containing a number of carbon atoms ranging from 1 to 12, a phenyl radical, or an aralkyl radical containing, for example, from 1 to 10 carbon atoms. By way of illustration of such monovalent radicals, mention will be made of ethyl, butyl, tert-butyl and isopropyl radicals.

According to the present invention, the alkoxyamines of formula (I) in which n=2 and in which at least one of the remaining valencies on the carbon atom bearing $R_L$ is linked to a hydrogen atom, are most particularly preferred.

The two remaining valencies on the carbon atom may also be linked to a divalent radical so as to form a ring including the carbon atom bearing the radical $R_L$, said ring possibly containing a number of carbon atoms ranging from 3 to 10 and possibly containing a hetero atom such as N, O or S.

The remaining valency on the nitrogen atom may also be linked to a group —C(CH$_3$)$_2$Z with Z=—COOalkyl, —COOH, —CH$_3$, —CN, —CH$_2$OH, —CH$_2$OSi(CH$_3$)$_3$.

The polyalkoxyamines of formula (I) may be prepared according to methods known in the literature. The method most commonly used involves the coupling of a carbon-based radical with a nitroxide radical. The coupling may be performed using a halo derivative $A(X)_n$ in the presence of an organometallic system, for instance CuX/ligand (X=Cl or Br) according to a reaction of ATRA (Atom Transfer Radical Addition) type as described by D. Greszta et al. in Macromolecules 1996, 29, 7661–7670.

This method consists in transferring an atom or a group of atoms to another molecule in the presence of an organometallic system CuX/ligand in a solvent medium, according to the scheme:

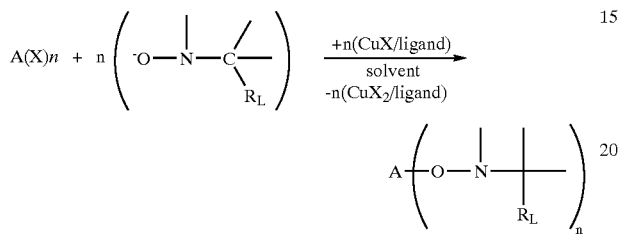

One procedure which is generally used consists in dissolving the organometallic system such as CuBr/ligand in an organic solvent which is preferably aromatic, such as benzene or toluene, and then in introducing into the solution the compound $A(X)_n$ and the β-substituted nitroxide

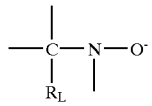

As examples of ligands used, mention will be made of bipyridine, 4,4'-bis(5-nonyl)-2,2'-bipyridine and tris(2-pyridylmethyl)amine (TPA).

The reaction mixture is then stirred at a temperature between 20° C. and 90° C. for a period which may be up to 48 hours, or even more.

Next, the precipitate is filtered off, rinsed with a solvent such as ether and the filtrate is then washed with an aqueous solution containing 5% by weight of $CuSO_4$ and then finally with water. The resulting solution is dried over magnesium sulfate and the solvents are then evaporated off under reduced pressure.

According to another particular advantageous procedure, a metal salt MX such as CuX, a ligand, the compound $A(X)_n$ and the β-substituted nitroxide:

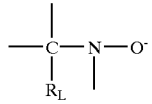

are mixed together with stirring in an organic solvent, in a β-substituted nitroxide/$A(X)_n$ molar ratio ranging from n to 2n, the reaction medium is kept stirring at a temperature of between 20° C. and 90° C. until the β-substituted nitroxide has disappeared, the organic phase is recovered and washed with water, and the polyalkoxyamine (I) is then isolated by evaporating off the organic solvent under reduced pressure.

As examples of ligands which may be used according to this procedure, mention will be made of:

tris[2-(dimethylamino)ethyl]amine:

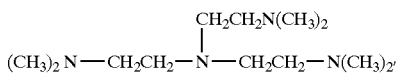

N,N,N',N',N"-pentamethyldiethylenetriamine (PMDETA):

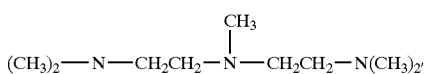

N,N,N',N'-tetramethylethylenediamine:

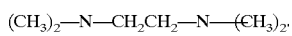

1,1,4,7,10,10-hexamethyltriethylenetetramine (HMTETA):

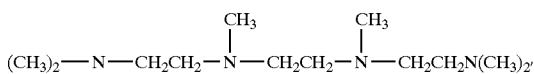

cyclic polyamines such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane.
PMDETA will preferably be used.

The oxidation state of the active species of metal M of the metal salt is equal to 1 (M').

This active species may be added as is to the reaction medium, preferably in the form of a metal halide such as CuBr.

The active species may also be generated in situ according to the redox reaction:

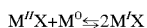

using a metal salt M"X such as $CuBr_2$ in which the metal M is in oxidation state 2 (M") and the same metal in oxidation state zero ($M^0$).

A metal salt MX in which the metal M is in oxidation state 1 (M'A) and the same metal M in oxidation state 0 ($M^0$) may also be introduced into the reaction medium.

According to this procedure, the ligand is used in a ligand/M' molar ratio ranging from 1 to 5 and preferably ranging from 1 to 2.

The β-substituted nitroxide/$A(X)_n$ molar ratio ranges from n to 1.4n and preferably is in the region of 1.

As illustrations of β-substituted nitroxides

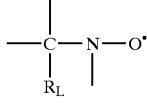

which may be used according to the present invention, mention will be made of:
N-tert-butyl-1-phenyl-2-methylpropyl nitroxide,
N-(2-hydroxymethylpropyl)-1-phenyl-2-methylpropyl nitroxide),
N-tert-butyl-1-diethylphosphono-2,2-dimethylpropyl nitroxide,
N-tert-butyl-1-dibenzylphosphono-2,2-dimethylpropyl nitroxide, N-tert-butyl-1-bis(2,2,2-trifluoroethyl)phosphono-2,2-dimethylpropyl nitroxide, N-tert-butyl[(1-diethylphosphono)-2-methylpropyl] nitroxide, N-(1-methylethyl)-1-cyclohexyl-1-(diethylphosphono) nitroxide, N-(1-phenylbenzyl)[(1-diethylphosphono)-1-methyethyl] nitroxide, N-phenyl-1-diethylphosphono-2,2-dimethylpropyl nitroxide, N-phenyl-1-diethylphosphono-1-methylethyl nitroxide, N-(1-phenyl-2-methylpropyl)-1-diethylphosphonomethylethyl nitroxide.

Most of the intermediate compounds $A(X)_n$ in which X represents a chlorine atom or a bromine atom, and which are capable of generating free radicals, are products that are either commercially available or are obtained according to methods described in the literature.

The compounds such as those represented by formula (IVi):

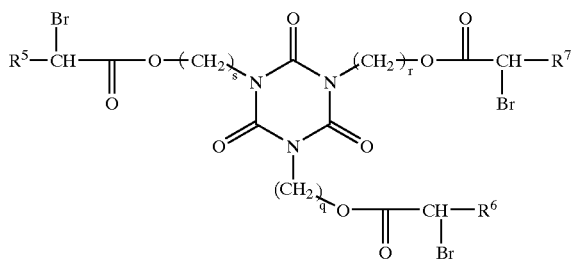
(IVi)

are novel compounds and, as such, form part of the present invention.

In this formula, $R^5$, $R^6$ and $R^7$, which may be identical or different, represent a linear or branched alkyl radical containing a number of carbon atoms ranging from 1 to 10, a phenyl radical, a benzyl radical, a cycloalkyl radical containing a number of carbon atoms ranging from 3 to 12, and q, r and s are integers ranging from 1 to 5.

The compounds of formula (IVi) according to the present invention were prepared according to a method which consists in introducing an acid bromide of formula (XI):

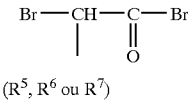
(XI)

($R^5$, $R^6$ or $R^7$)
with a 1,3,5-tris(α-hydroxyalkyl)cyanuric acid in an acid bromide/cyanuric acid derivative molar ratio which is substantially equal to 3, in heating the reaction medium at a temperature between 50° C. and 100° C., which is maintained for about 12 hours. After cooling to room temperature, the reaction medium is taken up in a halogenated solvent such as $CH_2Cl_2$ and washed with water till neutral.

The resulting solution is dried over $MgSO_4$ and the solvent is removed under reduced pressure.

The compounds obtained are identified by mass spectrometry and by $^1H$ and $^{13}C$ NMR.

The polyalkoxyamines of formula (I) according to the present invention may be used for the polymerization and copolymerization of any monomer containing a carbon-carbon double bond, which is capable of undergoing free-radical polymerization. The polymerization or copolymerization is performed under the usual conditions known to those skilled in the art, taking into account the monomer(s) under consideration. Thus, the polymerization or copolymerization may be performed in bulk, in solution, in emulsion or in suspension, at temperatures ranging from 50° C. to 250° C. and preferably ranging from 70° C. to 150° C. As nonlimiting examples of monomers which may be used according to the present invention, mention will be made of vinylaromatic monomers such as styrene, substituted styrenes, dienes, acrylic monomers such as alkyl or aryl acrylates and methacrylates, optionally containing fluorine, for instance methyl acrylate, butyl acrylate or methyl methacrylate, and acrylamides such as N,N-dimethylacrylamide. The monomer may also be vinyl chloride, vinylidene difluoride or acrylonitrile.

The nitroxide—optionally corresponding to the polyalkoxyamine (I) used—may optionally be added to the polymerization medium, in a nitroxide/polyalkoxyamine (I) molar ratio ranging from 0.01n % to 20n % preferably ranging from n % to 10n %.

The polyalkoxyamines (I) according to the present invention may also be used for the synthesis of "sequenced" block copolymers according to a procedure which consists in carrying out, in a first step, the bulk, solution, suspension or emulsion polymerization of a monomer M1 or a mixture of monomers containing a carbon-carbon double bond capable of undergoing free-radical polymerization in the presence of a polyalkoxyamine (I) at a temperature ranging from 50° C. to 250° C. and preferably ranging from 70° C. to 150° C., and then, in a second step, allowing the temperature to fall and optionally evaporating off the residual monomer(s), and then, in a third step, in introducing the monomer M2 or a new mixture of monomers into the reaction medium obtained above, and then resuming the polymerization by simply raising the temperature.

By way of example, sequenced block copolymers such as polystyrene-polybutyl polyacrylate-polystyrene (PS-BUA-PS) may be prepared in this manner.

The examples which follow illustrate the invention.

GENERAL COMMENTS

The compounds obtained in the synthesis examples are identified by CHN microanalysis and by $^1H$, $^{13}C$ and $^{31}P$ NMR.

The β-substituted nitroxide used has the formula:

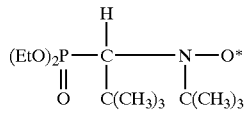

and will be denoted as DEPN.

It was obtained by oxidation of diethyl 2,2-dimethyl-1-(1,1-dimethylethylamino)propylphosphonate using meta-chloroperbenzoic acid according to a protocol described in International patent application WO 96/24620.

The general reaction used in Examples 1 to 9 is as follows:

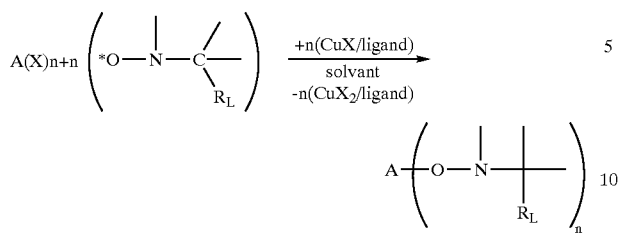

The polynitrogen ligands used are:
N,N,N',N',N"-pentamethyldiethylenetriamine, denoted hereinbelow as PMDETA,
tris(2-pyridylmethyl)amine, denoted hereinbelow as TPA,
bipyridine, denoted hereinbelow as BIPY.
A-$(X)_n$ denotes a polyfunctional core comprising n halo functions. We used polybromo or polychloro esters, except in Example 7 in which the following chloro phosphite was used:

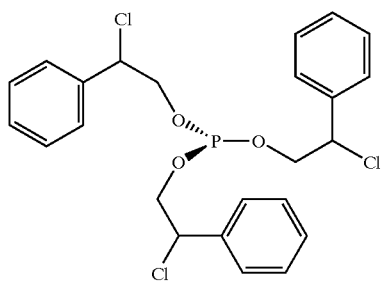

and in Example 8 in which para-bis(1-bromoethyl)benzene was used, obtained according to a conventional method by reacting diethylbenzene with two equivalents of N-bromosuccinimide.

In order to obtain chloro esters of Examples 3, 4 and 9, we used the following standard reaction:

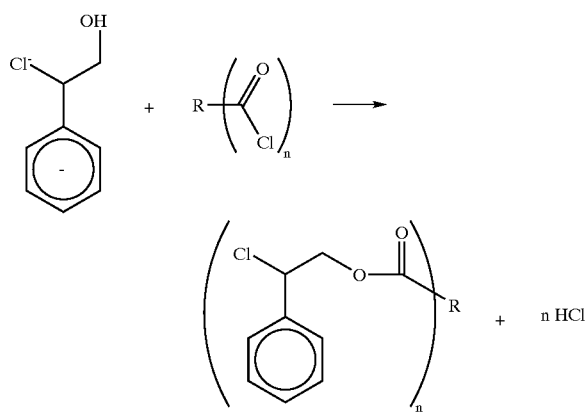

by directly reproducing the procedures known to those skilled in the art.

The bromo esters of Examples 1 and 2 are obtained in accordance with Example 251 of International patent application WO 98/40415.

The tribromo triester used in Example 5 is obtained by reacting 1,3,5-tris(2-hydroxyethyl)cyanuric acid with 2-bromopropionyl bromide and is described in Example 5.

The alkoxyamines A1 and A2 are those containing sequences of acrylate-DEPN type. Those denoted by a name of the type S1, S2, S3 or S4 contain sequences of phenylethyl-DEPN type.

EXAMPLE 1

Synthesis of the Dialkoxyamine A1

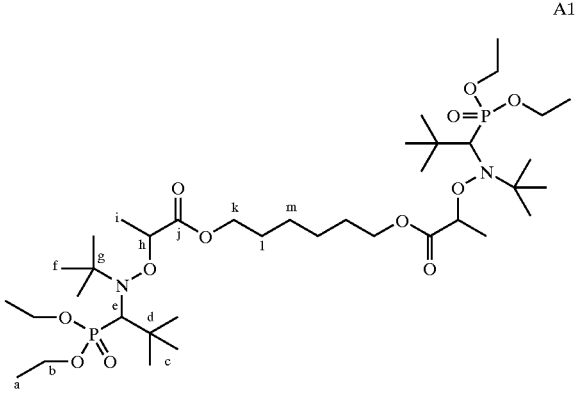

The reaction is carried out in a Schlenk tube under an argon atmosphere. The 1,6-hexanediol bis(2-bromopropionate) of formula:

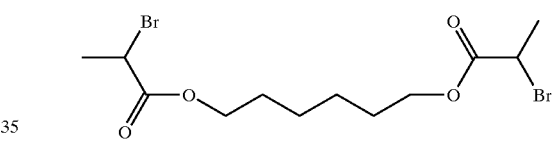

and the DEPN are degassed beforehand. The toluene is distilled under argon over sodium-benzophenone. 1.02 g of CuBr, 2.23 g of BIPY and 0.45 g of copper powder are introduced into the 100 ml Schlenk tube. The system is purged with vacuum-argon sequences and then 1.39 g of 1,6-hexanediol bis(2-bromo-propionate) and 3 g of 70% DEPN dissolved in 30 ml of toluene are then added. The mixture is left to react for 3.5 days at room temperature with stirring. The reaction is monitored by TLC (4/1 ether/heptane eluent). At the end of the reaction, the reaction mixture is filtered through Celite. The filtrate is washed with aqueous 5% copper sulfate solution and then with water. The organic phase is dried over magnesium sulfate and the solvent is then evaporated off (crude mass=2.93 g).

The product is purified by chromatography on a column of silica using a 4/1 ether/heptane and then a 1/1 ether/methanol eluent. From 0.96 g used, 0.73 g of a colorless oil is recovered.

The overall yield of isolated product is 75%.

Elemental analysis: ($C_{38}H_{78}N_2O_{12}P_2$): calculated: C 55.9%; H 9.6%; N 3.4%; found: C 55.41%; H 9.54%; N 3.58%.

$^1$H, $^{13}$C and $^{31}$P NMR: the product shows four asymmetric carbon atoms and one center of symmetry. The NMR signals are complex and reveal two distinct families of isomers in 50/50 relative proportions. The $^1$H, $^{13}$C and $^{31}$P chemical shifts (solvent=CDCl$_3$) are given in Table 1. The various atoms are referred to by an index indicated in the structural formula A1 above. When the signals are distinct, the two families of isomers are separated by a ";".

TABLE 1

| POSITION | $^1$H NMR | $^{13}$C NMR | P$^{31}$ NMR |
|---|---|---|---|
| a | 1.3 (broad, 12 H) | 16.5; 16.9 | |
| b | 3.7–4.4 (broad, 8 H) | 64.9–59.7; 65.0–59.9 | |
| c | 1.11–1.12 (18 H) | 30.2; 29.78 | |
| d | | 36.0; 35.67 | |
| e | 3.39; 3.31 ($J_{PH}^2$ = 32 Hz) | 68.8; 70.1 (d, $J_{PC}^2$ = 140 Hz) | |
| f | 1.17–1.2 (broad, 18 H) | 28.3 | |
| g | | 62.0; 62.2 | |
| h | 4.59 (m, $J_{HH}^3$ = 3 Hz, 2H) | 83.3; 77.6 | |
| i | 1.49; 1.50 (d, $J_{HH}^3$ = 3 Hz, 6 H) | 19.7; 18.3 | |
| j | | 172.5; 174.9 | |
| k | 3.7–4.7 (broad, 4 H) | 62.7; 62.6 | |
| l | 1.67 (4 H) | 26.0 | |
| m | 1.41 (4 H) | 28.8 | |
| P atom | — | — | 21.59–21.61, 21.14–21.26 |

EXAMPLE 2

Access to the Dialkoxyamine A1 With PMDETA as Amine Ligand Instead of BIPY

The procedure is the same as in Example 1. The ratios of reagents used are: DEPN/dibromo diester=2, CuBr/dibromo diester=2, PMDETA/CuBr=2, Cu(O)/CuBr=1.

The PMDETA ligand allows the reaction time to be reduced to 3 hours.

The purification is carried out by washing the reaction mixture with water after filtration (until a colorless aqueous phase is obtained). The product is in the form of a colorless oil.

The weight yield is quantitative.

EXAMPLE 3

Synthesis of Dialkoxyamine S1

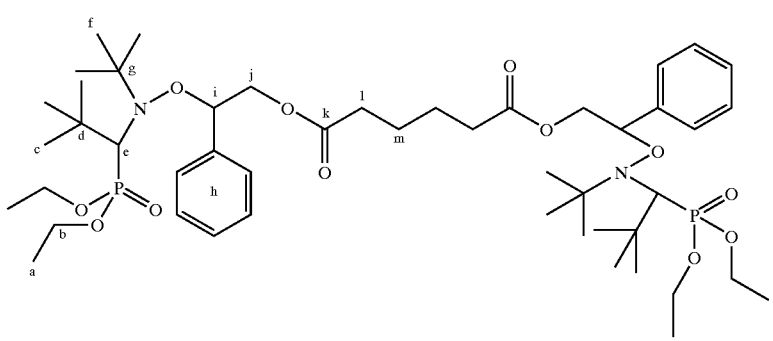

S1

The reaction is carried out in a Schlenk tube under an argon atmosphere. The bis β-chlorophenethyl adipate of formula:

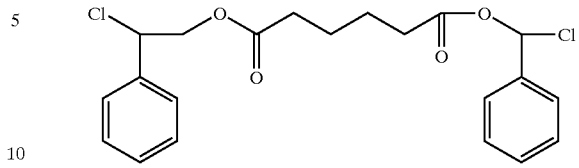

and the DEPN are degassed beforehand. The toluene is distilled under argon over sodium-benzophenone.

3.25 g of CuBr, 7.8 g of PMDETA and 1.29 g of copper powder are introduced into the 100 ml Schlenk tube. The system is purged with vacuum-argon sequences and 5 g of bis(β-chlorophenethyl) adipate (11.4 mmol) and 7.5 g of 90% DEPN dissolved in 50 ml of toluene are then added. The mixture is left to react for 12 hours at room temperature. The reaction is monitored by TLC (4/1 ether/heptane eluent). At the end of the reaction, the reaction mixture is filtered through Celite. The filtrate is washed with water. The solvent is evaporated off and the expected dialkoxyamine S1 is recovered in the form of a colorless oil (mixture of diastereoisomers). Quantitative yield.

Elemental analysis: $C_{48}H_{82}N_2O_{12}P_2$: calculated: C 61.3%; H 8.8%; N 3.0%; found: C 61.41%; H 8.62%; N 2.95%.

$^1$H, $^{13}$C, $^{31}$P NMR: the spectra show that by NMR there are two distinct families of isomers in a 63/37 relative proportion. Table 2 summarizes the chemical shifts of the hydrogen, carbon and phosphorus atoms indexed as on the structural formula S1. The shifts corresponding to the predominant isomer family are underlined when they are distinguished from the others.

TABLE 2

| POSITION | $^1$H NMR | $^{13}$C NMR | $^{31}$P NMR |
|---|---|---|---|
| a | 1.2 (broad) | 16.1–16.3; 16.2–16.7 | |
| b | 3.7 to 4.5 (m, 8H) | 58.8–59.1; 61.5 | |
| c | 1.2 (broad) | 30.7; 30.0 | |
| d | / | 35.3; 35.7 | |
| e | 3.35; 3.40(2 H; | 69.7; 69.3 | |

TABLE 2-continued

| POSITION | $^1$H NMR | $^{13}$C NMR | $^{31}$P NMR |
|---|---|---|---|
| | J2HP = 25 Hz) | (J$^1$CP = 139 Hz) | |
| f | 1.2 (broad) | 27.9 | |
| g | / | 67.8 | |
| h | 7.2 (1.0 H, H arom.) | 128.6–138.9 | |
| i | 5.29; 5.03 | 79.7; 86.7 | |
| j | 4.45–4.90 | 64.6; 65.8 | |
| k | / | 171.2 | |
| l | 1.85–2.25 | 33.5; 33.6 | |
| m | 1.85–2.25 | 23.9; 23.8 | |
| P atom | / | / | 24.2; 25.3 |

EXAMPLE 4

Synthesis of Dialkoxyamine S2

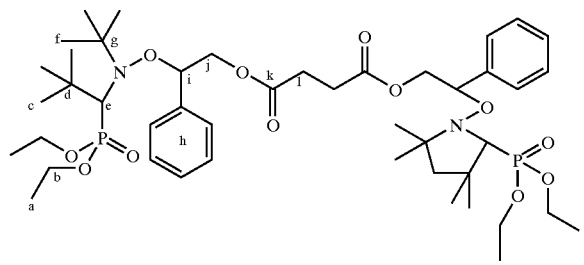

S2

The reaction is carried out in a Schienk tube under an argon atmosphere. The bis(β-chlorophenethyl) succinate of formula:

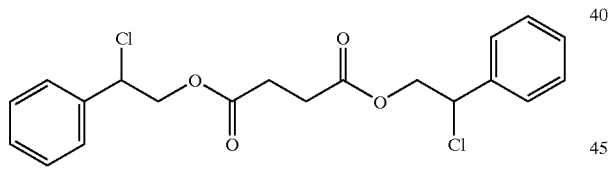

and the DEPN are degassed beforehand. The toluene is distilled under argon over sodium-benzophenone.

3.25 g of CuBr, 7.8 g of PMDETA and 1.29 g of copper powder are introduced into the 100 ml Schlenk tube. The system is purged with vacuum-argon sequences and 4.66 g of bis(β-chlorophenethyl) succinate (11.4 mmol) and 7.5 g of 90% DEPN dissolved in 50 ml of toluene are then added. The mixture is left to react for 12 hours at room temperature with stirring. The reaction is monitored by TLC (4/1 ether/heptane eluent). At the end of the reaction, the reaction mixture is filtered through Celite. The filtrate is washed with water. The solvent is evaporated off and the expected product is recovered in the form of a colorless oil (mixture of diastereoisomers). Quantitative yield.

Elemental analysis: $C_{46}H_{78}N_2O_{12}P_2$: calculated: C 60.5%; H 8.6%; N 3.1% found: C 60.45%; H 8.58%; N 3.2%.

NMR:

The spectra show that by NMR there are two distinct families of isomers in a 60/40 relative proportion. Table 3 summarizes the chemical shifts of the hydrogen, carbon and phosphorus atoms indexed as on the structural formula. The shifts corresponding to the predominant family of isomers are underlined when they are distinguished from the others.

TABLE 3

| POSITION | $^1$H NMR | $^{13}$C NMR | $^{31}$P NMR |
|---|---|---|---|
| a | 1.2 (broad) | 16.1–16.3; 16.2–16.7 | |
| b | 3.7 to 4.4 (m, 8 H) | 58.8–61.6; 59.1–61.5 | |
| c | 1.2 (broad) | 30.7; 30.0 | |
| d | / | 35.2; 35.6 | |
| e | 3.34; 3.41(2H; J2HP = 25 Hz) | 69.6; 69.3 (J1CP = 140 Hz) | |
| f | 1.21 (broad) | 27.8; 28.5 | |
| g | / | 61.8; 61.6 | |
| h | 7.2–7.3 (10 H, H arom.) | 128.5–140.4 | |
| i | 5.28; 5.07 (2H) | 79.7; 86.7 | |
| j | 4.77–4.49; 4.4–4.90 (4 H) | 64.9; 66.3 | |
| k- | / | 171.4 | |
| l | 2.10–2.35 (4H) | 28.9; 28.8 | |
| P atom | / | / | 24.2; 25.3 |

EXAMPLE 5

Synthesis of Trialkoxyamine A2

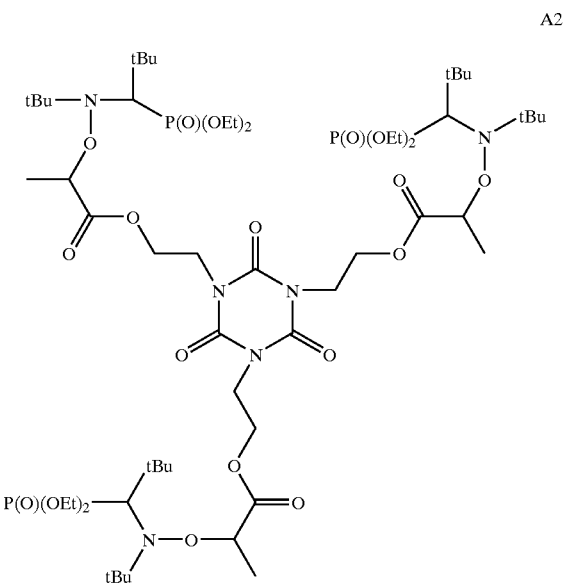

A2

The starting tribromo triester has the formula

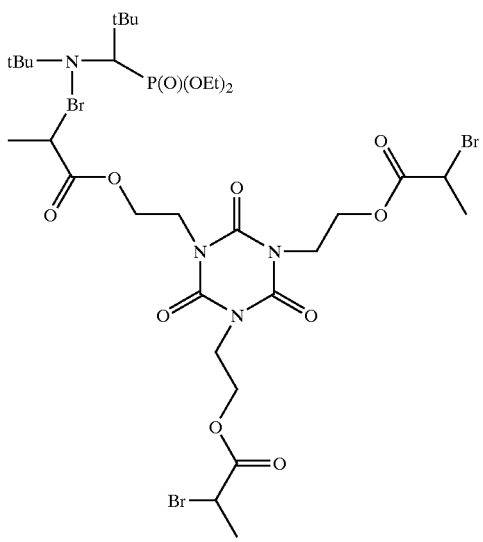

a) Synthesis of the Triester:

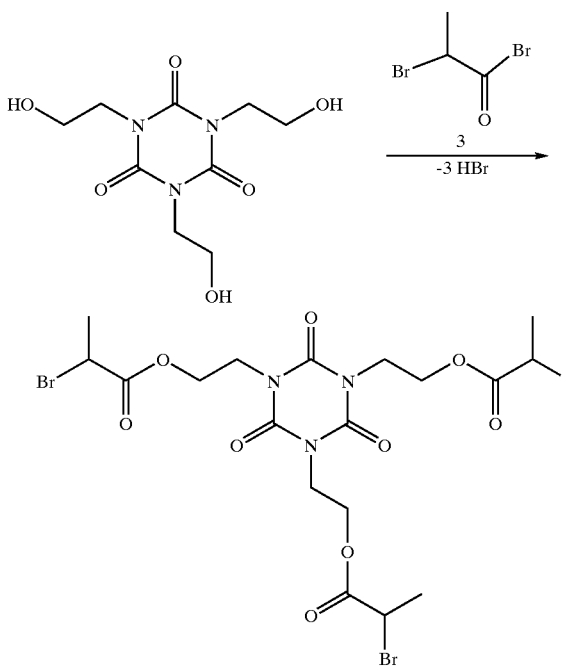

15 g of 1,3,5-tris(2-hydroxyethyl)cyanuric acid (57 mmol) are loaded into a 250 ml glass reactor. 37.1 g of 2-bromopropionyl bromide (172 mmol) are added dropwise and the mixture is then heated to 80° C. The reaction mixture is left to react overnight and is then taken up in dichloromethane and washed with water until neutral. The resulting solution is dried over magnesium sulfate and evaporated. 35.6 g of a virtually colorless syrup are thus obtained (weight yield=93%). The product was characterized by $^1$H and $^{13}$C NMR.

b) Synthesis of the Trialkoxyamine:

The reaction is carried out in a Schlenk tube under an argon atmosphere. The DEPN is degassed beforehand. The toluene is distilled under argon over sodium benzophenone.

1.03 g of CuBr, 2.09 g of TPA and 0.45 g of copper powder are introduced into the 100 ml Schlenk tube. The system is purged with vacuum-argon sequences and 1.6 g of tribromo triester synthesized in a) and 3.02 g of 70% DEPN dissolved in 10 ml of toluene are then added. The mixture is left to react for 1 hour at room temperature with stirring. The reaction mixture is filtered through Celite and the solvent is then evaporated off. 3.11 g of a crude product are obtained (as a colorless syrup).

The product is purified by chromatography on a column of silica, using an ether/ethanol eluent containing 1% ethanol. From 1 g used, 0.86 g of colorless syrup is recovered.

The overall yield isolated product is 82%.

The product was characterized by mass spectrometry and by $^1$H, $^{13}$C and $^{31}$P NMR. The NMR spectra show that there are two distinct families of isomers in a 50/50 relative proportion. The $^1$H and $^{31}$P chemical shifts (solvent=CDCl$_3$) are given in Table 4. The various atoms are referred to by index on the structural formula below. When the signals are distinct, the two families of isomers are separated by a ";".

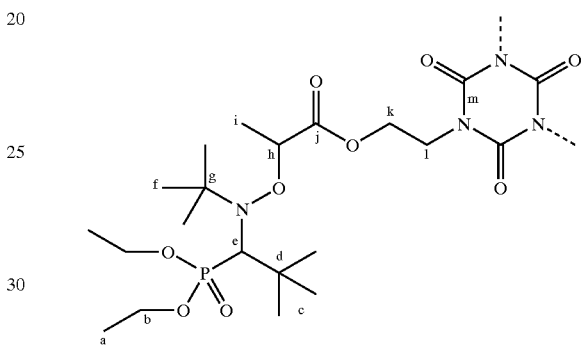

TABLE 4

| POSITION | $^1$H NMR | $^{31}$P NMR |
|---|---|---|
| a | 1.25 (broad, 18 H) | |
| b | 3.8–4.4 (broad, 12 H) | |
| c | 1.09; 1.12 (27 H) | |
| d | | |
| e | 3.27; 3.33 ($J_{PH}^2$ = 25 Hz, 3H) | |
| f | 1.17 (27 H) | |
| g | | |
| h | 4.58 (m, $J_{HH}^3$ = 3 Hz, 3 H) | |
| i | 1.49 (m, 9 H) | |
| j | | |
| k | 3.8–4.4 (broad, 6 H) | |
| l | 3.8–4.4 (broad, 6 H) | |
| P atom | — | 24.3–24.35–24.4; 24.95–25.0–25.05 |

EXAMPLE 6

Use of PMDETA to Synthesize the Trialkoxyamine A2

The conditions used are: DEPN/tribromo triester=3, CuBr/tribromo triester=3, PMDETA/CuBr=2, Cu(O)/CuBr=1, solvent=toluene, T=20° C., t=7 hours.

The product is purified by washing with water (5×500 ml).

The material balance is given in Table 5. The percentages of trialkoxyamine and of mono- and dialkoxyamine were determined by $^1$H and $^{31}$P NMR. The content of residual DEPN was determined by HPLC. The content of residual solvent was determined by $^1$H NMR.

TABLE 5

| REAGENTS | | |
|---|---|---|
| 95% tribromo triester | 55.0 g | 0.079 mol |
| 90% DEPN | 77.2 g | 0.236 mol |
| CuBr | 33.9 g | 0.236 mol |
| PMDETA | 81.9 g | 0.472 mol |
| Cu(O) | 15.0 g | 0.236 mol |
| Toluene | 800 ml | |
| Crude product | 95.9 g | |
| Weight yield | 93% | |
| Composition weight | (%) | |
| Trialkoxyamine A2 | 94 | |
| Di- + monoalkoxyamine | 3 | |
| Residual solvent | 3 | |
| Residual DEPN | <0.1 | (conversion = 99.9%) |

EXAMPLE 7

Synthesis of the Trialkoxyamine S3

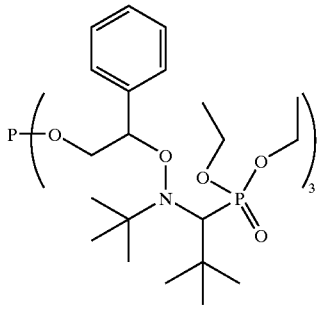

The reaction is carried out in a Schlenk tube under an argon atmosphere. The trichloro phosphite of formula:

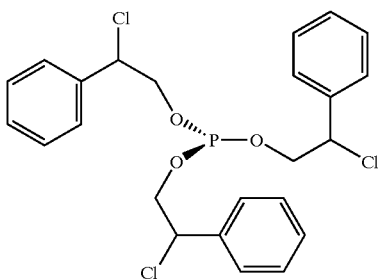

prepared from $PCl_3$ and styrene oxide according to a protocol described in U.S. Pat. No. 2,876,246, and the DEPN are degassed beforehand. The toluene is distilled under argon over sodium-benzophenone.

3.4 g of CuBr, 8.2 g of PMDETA and 1.5 g of copper powder are introduced into the 100 ml Schlenk tube. The system is purged with vacuum-argon sequences and 3.9 g of the phosphite (7.9 mmol) and 7.7 g of 90% DEPN dissolved in 50 ml of toluene are then added. The mixture is left to react for 12 hours at room temperature with stirring. The reaction is monitored by TLC (4/1 ether/heptane eluent). At the end of the reaction, the reaction mixture is filtered through Celite. The filtrate is washed with water. The solvent is evaporated off and the expected product is recovered in the form of a slightly yellow oil (mixture of diastereomers). Yield: 3.1 g, i.e. 31%.

Elemental analysis: $C_{63}H_{111}N_3O_{15}P_4$: calculated: C 59.4%; H 8.8%; N 3.3% found: C 59.01%; H 8.59%; N 3.21%.

EXAMPLE 8

Synthesis of the Dialkoxyamine S4

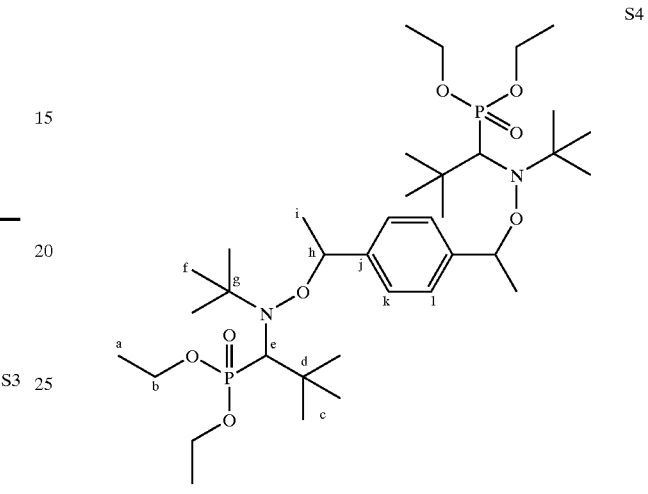

The reaction is carried out in a Schlenk tube under an argon atmosphere. The para-bis(1-bromoethyl)benzene and the DEPN are degassed beforehand. The toluene is distilled under argon over sodium-benzophenone.

1.02 g of CuBr, 3 ml of PMDETA (i.e. 4 eq.) and 0.5 g of copper powder are introduced into the 100 ml Schlenk tube. The system is purged with vacuum-argon sequences and 1.03 g of para-bis(1-bromoethyl)-benzene (3.53 mmol) and 1.77 g of 88% DEPN dissolved in 20 ml of benzene are then added. The mixture is left to react for 6 hours at room temperature with stirring. The reaction is monitored by TLC (4/1 ether/heptane eluent). At the end of the reaction, the reaction mixture is filtered over Celite after addition of ether. The filtrate is washed with water. The solvent is evaporated off and an oil is recovered, which is purified by chromatography on a column of silica (eluent: 6/4 pentane/ethyl acetate). The column does not allow separation of the various diastereoisomers detected by phosphorus NMR and mass spectrometry. Yield: 1.9 g, i.e. 78%.

Elemental analysis: $C_{36}H_{70}N_2O_8P_2$: calculated: C 59.98%; H 9.79%; N 3.88% found: C 59.96%; H 9.87%; N 3.94%.

In a conventional manner, the $^{31}P$ NMR shows two families of peaks corresponding to two types of diastereoisomer.

$^{31}P$ NMR: first family δ=23.05–23.09–23.21; second family: 24.36–24.4.

After one night at 0° C., one of the diastereoisomers crystallizes and may be recovered in the form of white crystals: m.p.=148° C.

The complete NMR analysis of this diastereoisomer was able to be performed, and consists of the diastereoisomer having a phosphorus NMR chemical shift of 23.2 ppm. The $^1H$ and $^{13}C$ chemical shifts are given in Table 6.

TABLE 6

| POSITION | $^1$H NMR | $^{13}$C NMR |
|---|---|---|
| a | 0.89 (t, J2HH = 7.08 Hz, 12 H) | 16.4 |
| b | 3.2–3.5; 3.75–4.10 (broad, 8 H) | 58.9 and 61.7 (d, JPC = 7.19 and 6.1 Hz) |
| c | 1.2–1.3 (broad; 36 H with f) | 28.3 |
| d | | 35.4 (d, JPC = 4.9 Hz) |
| e | 3.39 (J2PH = 26 Hz, 2 H) | 70.1 (d, JPC = 139 Hz) |
| f | see c | 30.7 (d, JPC = 5.9 Hz) |
| g | | 61.3 |
| h | 5.22 (q, J3HH = 6.5 Hz 2 H) | 78.2 |
| i | 1.51 (d, J3HH = 6.5 Hz 6 H) | 21.3 |
| j | | 142.5 |
| k and l | 7.44 (s, 4 H with 1) | 127.4 |

EXAMPLE 9

Synthesis of the Dialkoxyamine AS1

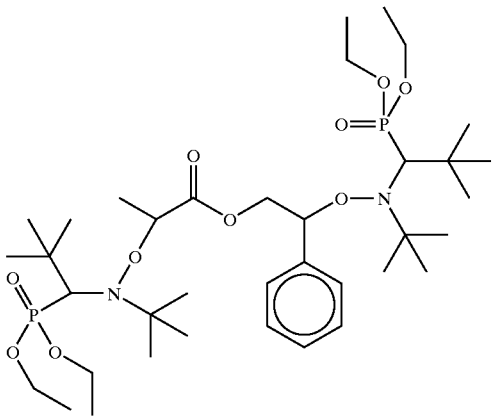

AS1

The reaction is carried out in a Schlenk tube under an argon atmosphere. The following dichloro ester:

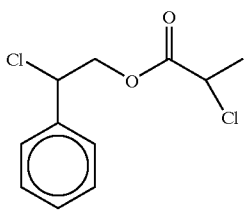

and the DEPN are degassed beforehand. The toluene is distilled under argon over sodium-benzophenone.

2.86 g of CuBr, 6.9 g of PMDETA and 1.2 g of copper powder are introduced into the 100 ml Schlenk tube. The system is purged with vacuum-argon sequences and 2.46 g of the dichloro ester (10 mmol) and 6.44 g of 90% DEPN dissolved in 40 ml of toluene are then added. The mixture is left to react for 12 hours at room temperature with stirring. The reaction is monitored by TLC (4/1 ether/heptane eluent). At the end of the reaction, the reaction mixture is filtered through Celite. The filtrate is washed with water. The solvent is evaporated off and the expected product is recovered in the form of a slightly yellow oil (mixture of diastereoisomers). Yield: 6.9 g, i.e. 90%.

Analysis

Elemental analysis: $C_{37}H_{70}N_2O_{10}P_2$: calculated: C 58.1%; H 9.2%; N 3.7% found: C 58.15%; H 9.35%; N 3.6%.

EXAMPLES OF CONTROLLED FREE-RADICAL POLYMERIZATION USING THE POLYALKOXYAMINES OF THE PRESENT INVENTION

The polymerizations were carried out under the following conditions:

Styrene or butyl acrylate are distilled and stored under an inert atmosphere at 5° C.

–1° The polyalkoxyamine and a monomer or a mixture of monomers are introduced into a Schlenk tube which has been predried under vacuum. The mixture is degassed by sparging with nitrogen for 20 minutes, and is then brought to the polymerization temperature. Samples are withdrawn using a syringe purged with nitrogen.

Analyses:

The number-average masses (Mn) and the polydispersity indices (Ip) were measured by steric exclusion chromatography (SEC). The chromatograms were recorded using a Spectra Physics machine fitted with an SP8810 pump, a Shodex RE-61RI differential refractometer, two PIgel mixed D columns (eluent: THF, 30° C.). The calibrations were carried out with standard polystyrene samples. The polystyrenes obtained are analyzed directly relative to these references, whereas the polybutyl acrylates are measured according to the universal calibration method.

The conversion was measured both by the SEC and $^1$H Nuclear Magnetic Resonance spectra on a Bruker 200 MHz spectrometer.

The examples which follow are defined by the following parameters: mass of monomer, mass of alkoxyamine, target theoretical molar mass (Mn(th)), temperature.

The results of each experiment are characterized by the reaction time, the conversion, the Mn(ex) of the polymer and the polydispersity index Ip. In certain cases, the curves indicating the conversion as a function of time and the Mn as a function of the conversion are reported.

A) BULK POLYMERIZATION OF STYRENE

EXAMPLE 1A

Polymerization Compound A1

| Data: | mass of dialkoxyamine A1: 1 g; mass of styrene: 48 g Mn(Th) = 40 000 g/mol; T = 123° C. |
|---|---|

The results are given in Table 7.

TABLE 7

| Time (min) | ln(M°/M) | Conversion (%) | Mn(Th) (g/mol) | Mn(ex) (g/mol) | MnTh/Mnex |
| --- | --- | --- | --- | --- | --- |
| 30 | 0.4 | 33 | 13 200 | 12 000 | 1.1 |
| 60 | 0.6 | 45 | 18 000 | 15 000 | 1.2 |
| 90 | 0.82 | 56 | 22 400 | 18 500 | 1.21 |
| 120 | 1.12 | 67 | 26 800 | 21 500 | 1.25 |
| 150 | 1.43 | 76 | 30 400 | 24 500 | 1.24 |
| 180 | 1.6 | 80 | 32 000 | 26 000 | 1.23 |

The polydispersity index Ip at the end of polymerization is 1.3.

The curve Mn as a function of the conversion—FIG. 1—shows that the polymerization with the dialkoxyamine A1 is well controlled. In this FIG. 1:

—O—O— represents MnTh
—X— represents Mn(ex).

EXAMPLE 2A

| Data: | Polymerization with compound A2: mass of trialkoxyamine A2: 1 g; mass of styrene: 45 g Mn(Th) = 60 000 g/mol; T = 123° C. |
| --- | --- |

The results are given in Table 8.

TABLE 8

| Time (min) | ln(M°/M) | Conversion (%) | Mn(Th) (g/mol) | Mn(ex) (g/mol) | MnTh/Mnex |
| --- | --- | --- | --- | --- | --- |
| 30 | 0.35 | 30 | 18 000 | 20 000 | 0.9 |
| 60 | 0.6 | 45 | 27 000 | 30 000 | 0.9 |
| 90 | 0.8 | 55 | 33 000 | 32 500 | 1.02 |
| 120 | 1.05 | 65 | 39 000 | 40 000 | 0.98 |
| 150 | 1.22 | 70 | 42 000 | 44 000 | 0.95 |
| 180 | 1.55 | 79 | 47 400 | 59 000 | 0.8 |

Figure 2:
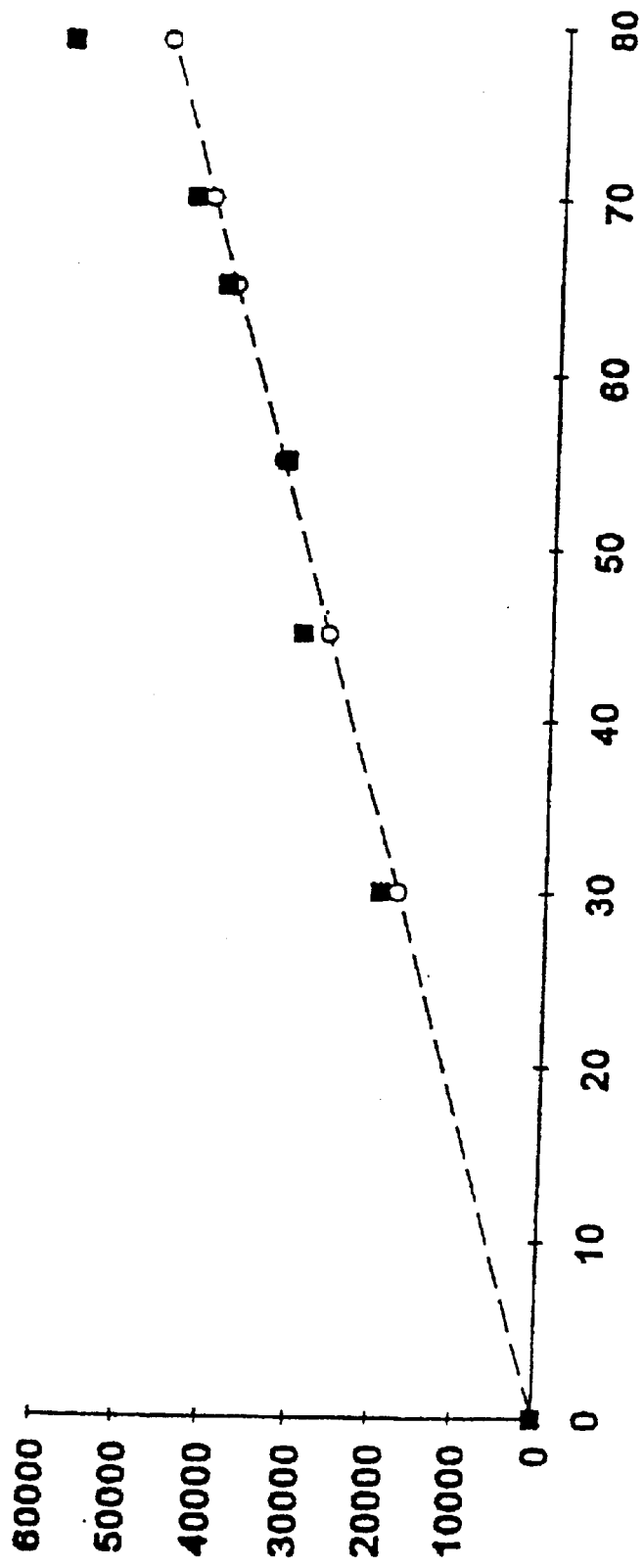

The polydispersity index Ip at the end of polymerization is: 1.4. The curve Mn as a function of the conversion—FIG. 2—clearly shows that the polymerization with the trialkoxyamine A2 is well controlled. In this FIG. 2:

—O— represents MnTh
■ represents Mn(ex).

EXAMPLE 3a

| Data: | Polymerization with the compound S4: mass of dialkoxyamine S4: 1 g; mass of styrene: 55 g Mn(Th) = 40 000 g/mol; T = 123° C. |
| --- | --- |

The results are given in Table 9.

TABLE 9

| Time (min) | ln(M°/M) | Conversion (%) | Mn(Th) (g/mol) | Mn(ex) (g/mol) | MnTh/Mnex |
| --- | --- | --- | --- | --- | --- |
| 0 | 0 | 0 | 0 | 0 | 0 |
| 30 | 0.32 | 27 | 10800 | 10500 | 1.03 |
| 60 | 0.52 | 41 | 16400 | 14500 | 1.13 |
| 90 | 0.7 | 50 | 20000 | 18000 | 1.11 |
| 120 | 0.84 | 57 | 22800 | 23000 | 0.99 |
| 150 | 1.09 | 66 | 26400 | 24500 | 1.08 |
| 180 | 1.4 | 75 | 30000 | 25500 | 1.18 |
| 210 | 1.65 | 81 | 32400 | 28500 | 1.14 |

Figure 3:
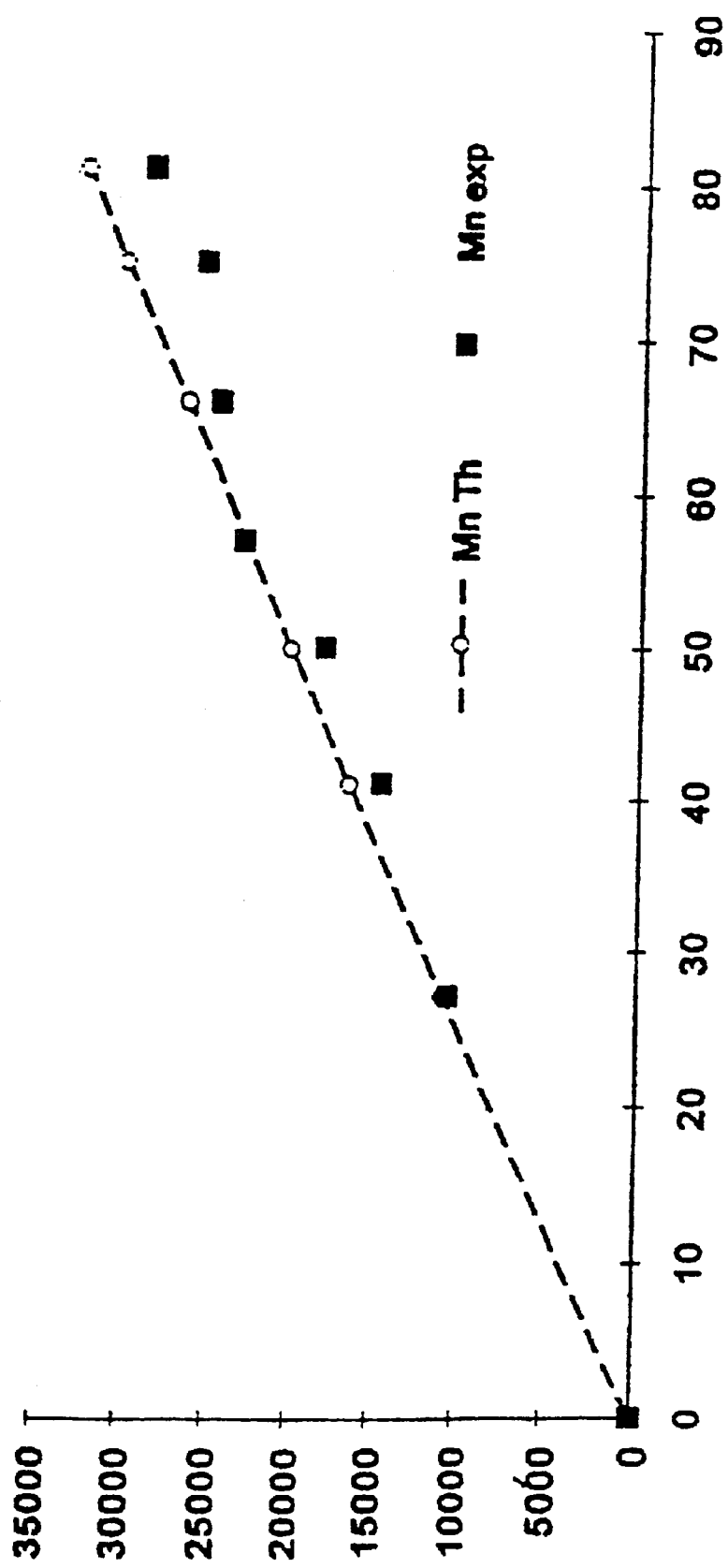

The polydispersity index at the end of polymerization is: 1.27. The curve Mn as a function of the conversion—FIG. 3—clearly shows that the polymerization with the trialkoxyamine S4 is well controlled. In this FIG. 3:

—O— represents MnTh,
■ represents Mn(ex).

EXAMPLE 4A

| Data: | Polymerization with the compound S1: mass of dialkoxyamine S1: 1 g; mass of styrene: 40 g Mn(Th) = 40 000 g/mol; T = 123° C. |
| --- | --- |
| Results: | After 3 hours, the sample withdrawn indicates a conversion of 83% for an Mn of 29 000 g/mol, i.e. Mn(th)/Mn(ex) = 1.14. Ip = 1.21. |

EXAMPLE 5A

| Data: | Polymerization with the compound S3 mass of trialkoxyamine: 1 g; mass of styrene: 46 g Mn(Th) = 60 000 g/mol; T = 123° C. |
| --- | --- |
| Results: | After 3 hours, the sample withdrawn indicates a conversion of 83% for an Mn of 50 500 g/mol, i.e. Mn(th)/Mn(ex) = 0.89. Ip = 1.36. |
| | B) BULK POLYMERIZATION OF BUTYL ACRYLATE (BUA) |

EXAMPLE 1B

| Data: | Polymerization with compound S4 mass of dialkoxyamine S4: 1 g; mass of BUA: 55 g Mn(Th) = 40 000 g/mol; T = 123° C. |
| --- | --- |

The results are given in Table 10.

TABLE 10

| Time (min) | ln(M°/M) | Conversion (%) | Mn(Th) (g/mol) | Mn(ex) (g/mol) | MnTh/Mnex |
| --- | --- | --- | --- | --- | --- |
| 0 | 0 | 0 | 0 | 0 | 0 |
| 30 | 0.8 | 55 | 22000 | 16000 | 1.38 |

TABLE 10-continued

| Time (min) | In(M°/M) | Conversion (%) | Mn(Th) (g/mol) | Mn(ex) (g/mol) | MnTh/Mnex |
|---|---|---|---|---|---|
| 60 | 1.1 | 67 | 26800 | 20000 | 1.34 |
| 90 | 2.3 | 90 | 36000 | 28500 | 1.26 |

The polydispersity index Ip at the end of polymerization is: 1.7.

C) IMPROVEMENT OF THE POLYMERIZATION OF BUTYL ACRYLATE (BUA) BY ADDING COMONOMER TO THE INITIAL MASS

In the following examples for obtaining a better control of the polymerization of butyl acrylate, we added 5% of styrene to the acrylate and we started the polymerization of this mixture.

EXAMPLE 1C

| Data: | Polymerization with the compound A1: mass of dialkoxyamine A1: 1 g; mass of butyl acrylate/styrene (95/5) mixture: 48 g Mn(Th) = 40 000 g/mol; T = 123° C. |
|---|---|

The results are given in Table 11.

TABLE 11

| Time (min) | In(M°/M) | Conversion (%) | Mn Th (g/mol) | Mn(ex) (g/mol) | MnTh/Mn(ex) |
|---|---|---|---|---|---|
| 0 | 0 | 0 | 0 | 0 | 0 |
| 30 | 0.45 | 36 | 14400 | 12000 | 1.2 |
| 60 | 0.8 | 55 | 22000 | 15000 | 1.47 |
| 90 | 1.35 | 74 | 29600 | 18500 | 1.6 |
| 120 | 1.71 | 82 | 32800 | 21500 | 1.53 |

Figure 4:
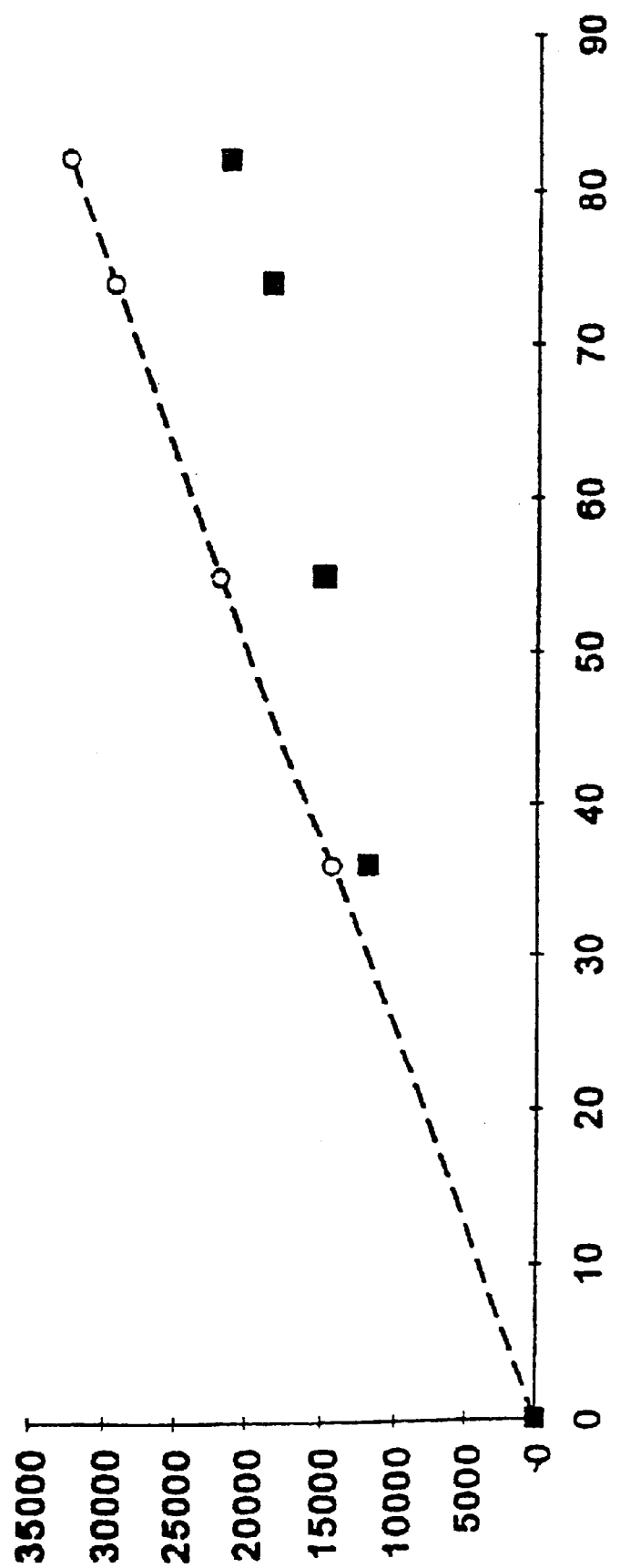

The polydispersity index Ip at the end of polymerization is: 1.4. The curve Mn as a function of the conversion—FIG. 4—clearly shows that the polymerization with the alkoxyamine A1 is well controlled. In this FIG. 4:

—O— represents MnTh

■ represents Mn(ex).

EXAMPLE 2C

| Data: | Polymerization with the compound A2: mass of trialkoxyamine A2: 1 g; mass of butyl acrylate/styrene (95/5) mixture: 45 g; Mn(Th) = 60 000 g/mol; T = 123° C. |
|---|---|

The results are given in Table 12.

TABLE 12

| Time (min) | In(M°/M) | Conversion(%) | Mn Th (g/mol) | Mn(ex) (g/mol) | MnTh/Mn(ex) |
|---|---|---|---|---|---|
| 0 | 0 | 0 | 0 | 0 | 0 |
| 30 | 0.55 | 42 | 25200 | 23000 | 1.1 |
| 60 | 1.1 | 67 | 40200 | 32000 | 1.26 |
| 90 | 1.6 | 80 | 48000 | 40000 | 1.2 |

Figure 5:
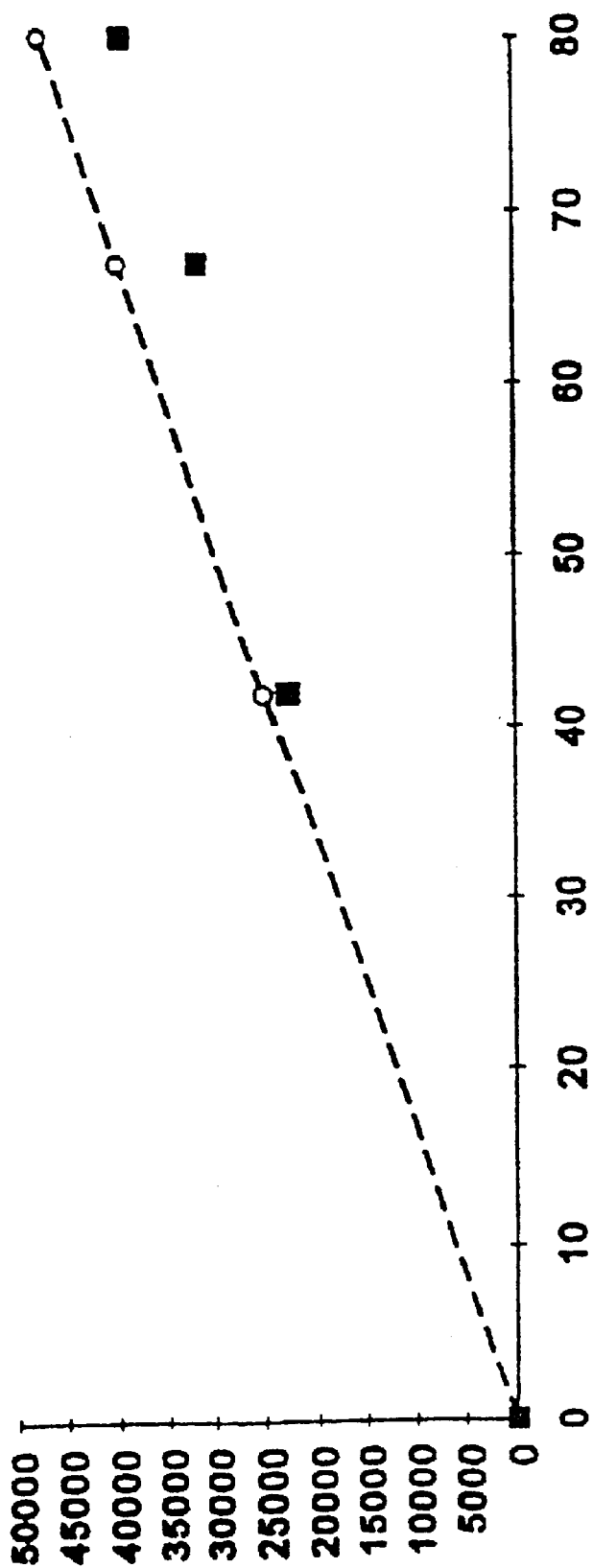

The polydispersity index Ip at the end of polymerization is: 1.4. The curve Mn as a function of the conversion—FIG. 5—clearly indicates that polymerization with the trialkoxyamine A2 is well controlled. In this FIG. 5:

—O— represents MnTh

■ represents Mn exp.

D) PRODUCTION OF A BLOCK COPOLYMER PS-PABU-PS

EXAMPLE 1D

Polymerization With the Compound A1

1st Block: polymerization according to Example 1c.

| Data: | mass of dialkoxyamine A1: 1 g; mass of butyl acrylate/styrene (95/5) mixture: 97 g Mn(Th) = 81 200 g/mol; T = 123° C. |
|---|---|
| Results: | After 2 hours, the temperature is allowed to fall. A 72% conversion (MnTh = 58 500) is obtained for an Mn of 55 300 (Mn(th)/Mn(exp) = 1.05) and a polydispersity index Ip = 1.3. |

The residual monomer is evaporated off under reduced pressure.

2nd Block:

The polymer obtained is diluted in styrene (260 g). The temperature of the reactor is raised to 123° C. The polymerization is then reviewed and is stopped after 30 min at 10% conversion such that the polystyrene blocks at the two ends of each chain have a length of 6 500 g/mol, i.e. an Mn(th)= 68 400 g/mol for the polymer.

Results:

Mn=73 900 g/mol (Mn(th)/Mn(exp)=0.93), Ip=1.7.

What is claimed is:

1. A compound of formula (I):

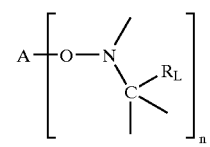

(I)

in which:

A represents a divalent or polyvalent structure;

$R_L$ represents a monovalent radical with a molar mass of greater than 15 and $n \geq 2$.

2. A compound according to claim 1, wherein

A is chosen from the following formulas II–IX:

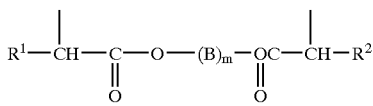
(II)

in which $R^1$ and $R^2$, which may be identical or different, are each a linear or branched alkyl radical containing 1 to 10 carbon atoms, a phenyl or thienyl radical which is optionally substituted with a halogen atom, a linear or branched alkyl radical containing 1 to 4 carbon atoms, nitro, alkoxy, aryloxy, carbonyl or carboxyl, a benzyl radical, or a cycloalkyl radical containing 3 to 12 carbon atoms, or a radical comprising one or more unsaturations; B is a linear or branched alkylene radical containing 1 to 20 carbon atoms; and m is an integer ranging from 1 to 10;

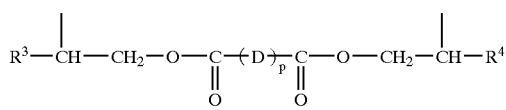
(III)

in which $R^3$ and $R^4$, which may be identical or different, are each aryl, pyridyl, furyl or thienyl which in each case is optionally substituted with a halogen atom, a linear or branched alkyl radical containing 1 to 4 carbon atoms, nitro, alkoxy, aryloxy, carbonyl or carboxyl; D is a linear or branched alkylene radical containing 1 to 6 carbon atoms, a phenylene radical or a cycloalkylene radical; and p is 0 to 10;

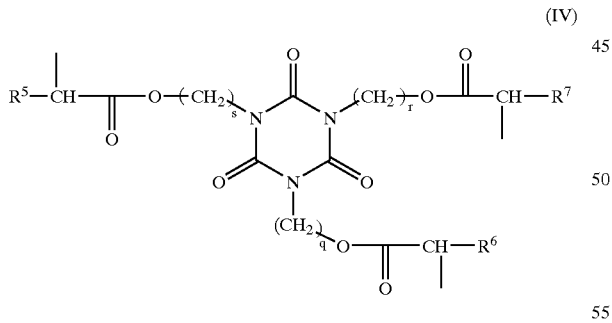
(IV)

in which $R^5$, $R^6$ and $R^7$, which may be identical or different, are each a linear or branched alkyl radical containing 1 to 10 carbon atoms, a phenyl or thienyl radical which is optionally substituted with a halogen atom, a linear or branched alkyl radical containing 1 to 4 carbon atoms, nitro, alkoxy, aryloxy, carbonyl or carboxyl, a benzyl radical, or a cycloalkyl radical containing 3 to 12, or a radical comprising one or more unsaturations; and q, r and s are each integers ranging from 1 to 5;

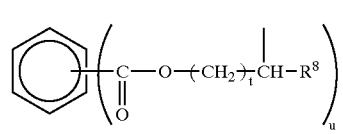
(V)

in which $R^8$ is aryl, pyridyl, furyl or thienyl which in each case is optionally substituted with a halogen atom, a linear or branched alkyl radical containing 1 to 4 carbon atoms, nitro, alkoxy, aryloxy, carbonyl or carboxyl, t is an integer ranging from 1 to 4, and u is $\geq 2$ and $\leq 6$;

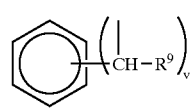
(VI)

in which $R^9$ is aryl, pyridyl, furyl or thienyl which in each case is optionally substituted with a halogen atom, a linear or branched alkyl radical containing 1 to 4 carbon atoms, nitro, alkoxy, aryloxy, carbonyl or carboxyl, and v is $\geq 2$ and $\leq 6$;

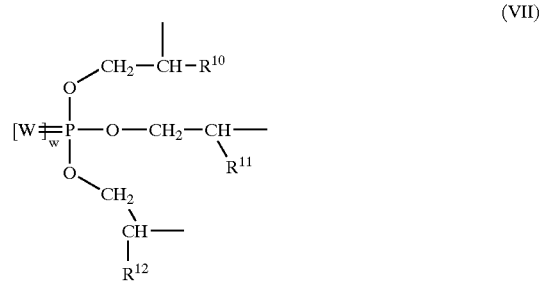
(VII)

in which $R^{10}$, $R^{11}$ and $R^{12}$, which may be identical or different, are each phenyl optionally substituted with a halogen atom, or a linear or branched alkyl radical containing 1 to 10 carbon atoms; W is an oxygen, sulfur or selenium atom, and w is equal to zero or 1;

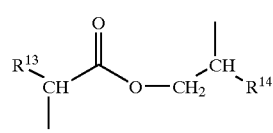
(VIII)

in which $R^{13}$ is a linear or branched alkyl radical containing 1 to 10 carbon atoms, a phenyl or thienyl radical which is optionally substituted with a halogen atom, a linear or branched alkyl radical containing 1 to 4 carbon atoms, nitro, alkoxy, aryloxy, carbonyl or carboxyl, a benzyl radical, or a cycloalkyl radical containing 3 to 12, or a radical comprising one or more unsaturations; and $R^{14}$ is aryl, pyridyl, furyl or thienyl which in each case is optionally substituted with a halogen atom, a linear or branched alkyl radical containing 1 to 4 carbon atoms nitro, alkoxy, aryloxy, carbonyl or carboxyl; and

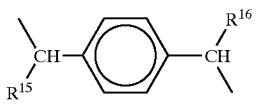
(IX)

in which $R^{15}$ and $R^{16}$, which may be identical or different, are each a hydrogen atom, a linear or branched alkyl radical containing 1 to 10 carbon atoms, or an aryl radical, optionally substituted with a halogen atom or a hetero atom.

3. A compound according to claim 1, wherein $R_L$ has a molar mass greater than 30.

4. A compound according to claim 3, wherein $R_L$ has a molar mass ranging from 40 to 450.

5. A compound according to claim 1, wherein the remaining valencies of the carbon atom bearing $R_L$ and of the nitrogen atom of formula (I) are linked to monovalent radicals or are linked together via a divalent radical so as to form a ring.

6. A compound according to claim 1, wherein the remaining monovalent radicals linked to the carbon atom bearing $R_L$ which may be identical of different, are a hydrogen atom, a linear or branched alkyl radical containing 1 to 12 carbon atoms, a phenyl radical or an aralkyl radical containing 1 to 10 carbon atoms.

7. A compound according to claim 1, wherein the remaining valency of the nitrogen is linked to a monovalent group —C(CH$_3$)$_2$Z wherein Z is —CO$_2$alkyl, —CO$_2$H, —CH$_3$, —CN, —CH$_2$OH or —CH$_2$OSi(CH$_3$)$_3$.

8. A compound according to claim 1, wherein $R_L$ comprises a phosphoryl group.

9. A compound according to claim 8, wherein $R_L$ is of the formula:

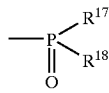
(X)

in which $R^{17}$ and $R^{18}$, which may be identical or different, are each a halogen, alkyl, cycloalkyl, alkoxy, aryloxy, aryl, aralkyloxy, perfluoroalkyl or aralkyl.

10. A compound according to claim 9, wherein $R^{17}$ and $R^{18}$ each contain 1 to 20 carbon atoms.

11. A compound according to claim 1, wherein in formula (I) n is 2 and at least one of the remaining valencies of the carbon atom bearing $R_L$ is linked to a hydrogen atom.

12. A polyalkoxyamine of formula:

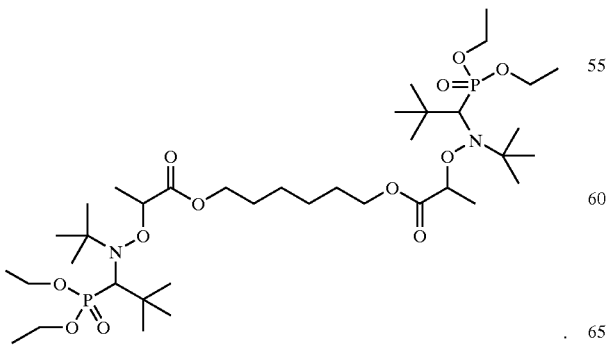

13. A polyalkoxyamine of formula:

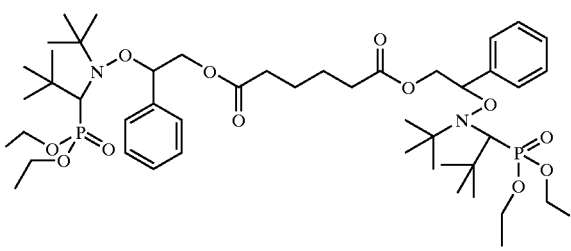

14. A polyalkoxyamine of formula:

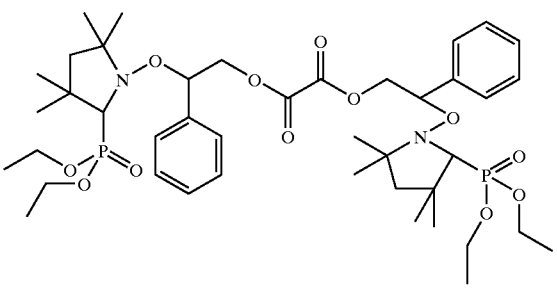

15. A polyalkoxyamine of formula:

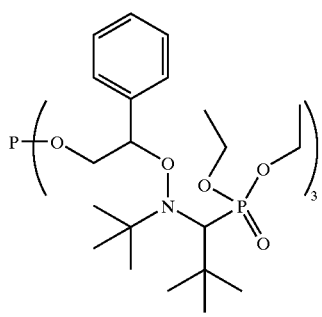

16. A polyalkoxyamine of formula:

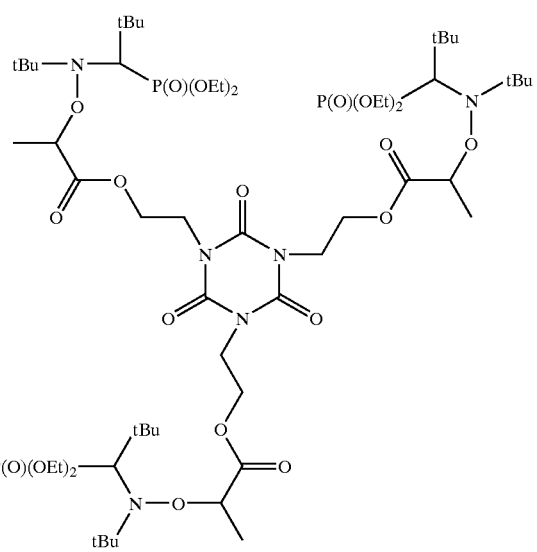

17. A polyalkoxyamine of formula:

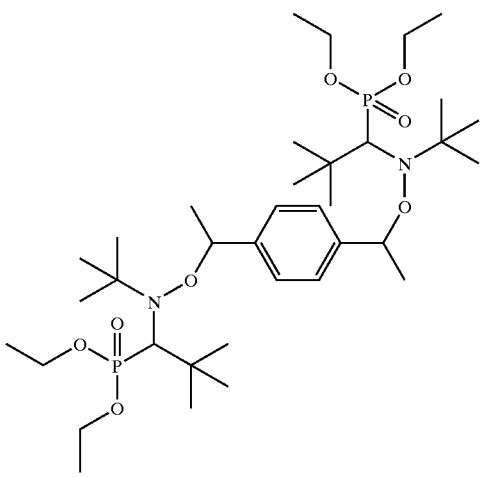

18. A polyalkoxyamine of formula:

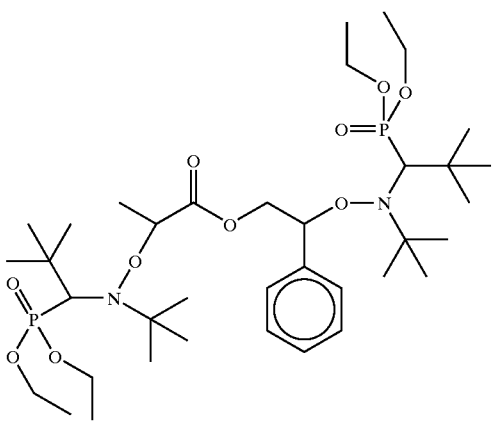

19. A compound of formula:

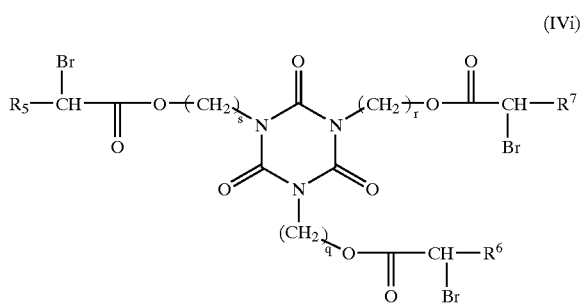

in which $R^6$, $R^7$ and $R^8$, which may be identical or different, are each a linear or branched alkyl radical containing 1 to 10 carbon atoms, a phenyl radical, a benzyl radical or a cycloalkyl radical containing 3 to 12 carbon atoms, and q, r and s are each integers ranging from 1 to 5.

20. A process comprising polymerizing at least one monomer containing a carbon-carbon double bond which is capable of undergoing bulk, solution, emulsion or suspension free radical polymerization, at a temperature of 50° C. to 250° C.,
wherein polymerization is performed in the presence of a compound according to claim 1, as a polymerization initiator.

21. A process as claimed in claim 20, wherein the polymerized monomer(s) is (are) vinylaromatic monomers optionally fluorinated acrylic monomers acrylamides or acrylonitrile.

22. A process as claimed in claim 20, wherein the polymerization is carried out in bulk.

23. A process as claimed in claim 20, wherein the polymerization is carried out in solution.

24. A process as claimed in claim 20, wherein the polymerization is carried out in emulsion.

25. A process as claimed in claim 20, wherein the polymerization is carried out in suspension.

26. A process as claimed in claim 20, wherein a further nitroxide, which does or does not correspond to a nitroxide from which the compound of formula (I) is obtained is also used.

27. A process as claimed in claim 26, wherein the nitroxide/polyalkoxyamine (I) molar ratio ranges from 0.01n % to 20n %.

28. A process as claimed in claim 20, wherein a mixture of monomers in variable proportions is polymerized.

29. A process as claimed in claim 28, wherein the mixture of monomers comprises at least one alkyl acrylate in a weight proportion of not more that 99.5%.

30. A process as claimed in claim 29, wherein the mixture of monomers is a mixture of alkyl acrylate and of a styrene olefin with a weight content of alkyl acrylate of between 88% and 97%.

31. A process as claimed in claim 29, wherein the alkyl acrylate is butyl acrylate.

32. A process as claimed in claim 20, wherein sequenced block copolymers are synthesized.

33. A process as claimed in claim 32, wherein the sequenced block copolymers are obtained according to a process which consists in carrying out, in a first step, polymerizing a monomer M1 or of a mixture of monomers containing a carbon-carbon double bond which is capable of undergoing a free-radical polymerization in the presence of a compound of formula (I) at a temperature ranging from 50° C. to 250° C.; and then, in a second step, allowing the temperature to fall, and optionally evaporating off unreacted residual monomer(s); and then, in a third step, introducing into the reaction medium a second monomer M2 or a new mixture of monomers; and then resuming polymerization by raising the temperature.

34. A process as claimed in claim 33, wherein M1 an optionally fluorinated alkyl acrylate and M2 is a styrene olefin.

35. A process as claimed in claim 33, wherein M1 is butyl acrylate and M2 is styrene.

36. A polymer or copolymer obtained as claimed in claim 20.

37. A process according to claim 20, wherein said monomer is a vinylaromatic monomer, a diene monomer, an acrylic monomer, an acrylamide monomer, vinyl chloride, vinylidene fluoride, or acrylonitrile.

38. A compound according to claim 1, wherein
the remaining monovalent radicals linked to the carbon atom bearing $R_L$, which may be identical of different, are each independently hydrogen, linear or branched alkyl containing 1 to 12 carbon atoms, phenyl, or aralkyl containing 1 to 10 carbon atoms;
the remaining valency of the nitrogen is linked to monovalent group —$C(CH_3)_2Z$ wherein Z is —$CO_2$alkyl, —$CO_2H$, —$CH_3$, —CN, —$CH_2OH$ or —$CH_2OSi(CH_3)_3$; and A is chosen from the structures below:

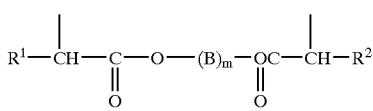
(II)

wherein $R^1$ and $R^2$, which may be identical or different, each represent linear or branched alkyl containing 1 to 10 carbon atoms, phenyl or thienyl which is optionally substituted by F, Cl, Br, linear or branched alkyl containing 1 to 4 carbon atoms, nitro, alkoxy, aryloxy, carbonyl or carboxyl, benzyl, or cycloalkyl containing 3 to 12 carbon atoms, and B is linear or branched alkylene containing 1 to 20 carbon atoms, and m is an integer ranging from 1 to 10;

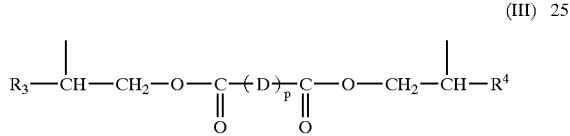
(III)

wherein $R^3$ and $R^4$, which may be identical or different, are each aryl, pyridyl, furyl or thienyl which in each case is optionally substituted by F, Cl or Br, linear or branched alkyl containing 1 to 4 carbon atoms, nitro, alkoxy, aryloxy, carbonyl or carboxyl, D is linear or branched alkylene containing 1 to 6 carbon atoms, phenylene or cycloalkylene, and p is 0 to 10;

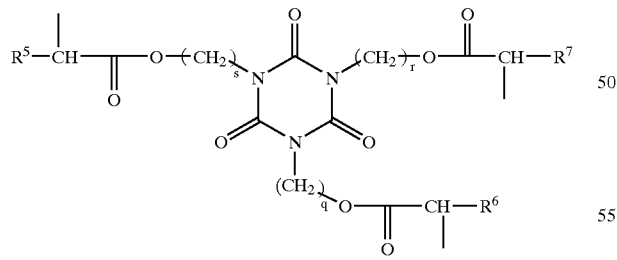
(IV)

wherein $R^5$, $R^6$ and $R^7$, which may be identical or different, each represent linear or branched alkyl containing 1 to 10 carbon atoms, phenyl or thienyl which is optionally substituted by F, Cl, Br, linear or branched alkyl containing 1 to 4 carbon atoms, nitro, alkoxy, aryloxy, carbonyl or carboxyl, benzyl, or cycloalkyl containing 3 to 12 carbon atoms, and q, r and s are each integers ranging from 1 to 5;

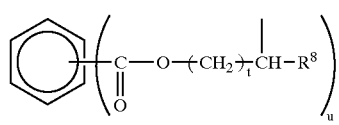
(V)

wherein $R^8$ is aryl, pyridyl, furyl or thienyl which in each case is optionally substituted by F, Cl or Br, linear or branched alkyl containing 1 to 4 carbon atoms, nitro, alkoxy, aryloxy, carbonyl or carboxyl, t is an integer ranging from 1 to 4, and u is $\geq 2$ and $\leq 6$;

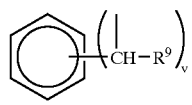
(VI)

wherein $R^9$ is aryl, pyridyl, furyl or thienyl which in each case is optionally substituted by F, Cl or Br, linear or branched alkyl containing 1 to 4 carbon atoms, nitro, alkoxy, aryloxy, carbonyl or carboxyl, and v is $\geq 2$ and $\leq 6$;

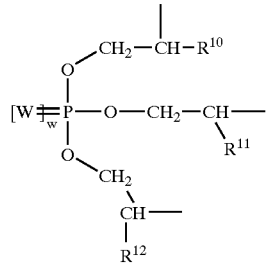
(VII)

wherein $R^{10}$, $R^{11}$ and $R^{12}$, which may be identical or different, are each phenyl which is optionally substituted by Cl or Br, or linear or branched alkyl containing 1 to 10 carbon atoms ranging from;

W is oxygen, sulfur or selenium, and w is equal to zero or 1;

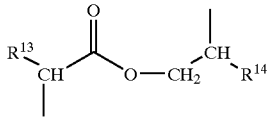
(VIII)

wherein $R^{13}$ is linear or branched alkyl containing 1 to 10 carbon atoms, phenyl or thienyl which is optionally substituted by F, Cl, Br, linear or branched alkyl containing 1 to 4 carbon atoms, nitro, alkoxy, aryloxy, carbonyl or carboxyl, benzyl, or cycloalkyl containing 3 to 12 carbon atoms, and R[14] is aryl, pyridyl, furyl or thienyl which in each case is optionally substituted by F, Cl or Br, linear or branched alkyl containing 1 to 4 carbon atoms, nitro, alkoxy, aryloxy, carbonyl or carboxyl; and

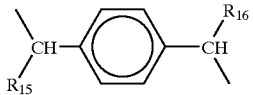
(IX)

wherein

R[15] and R[16], which may be identical or different, are each hydrogen, linear or branched alkyl containing 1 to 10 carbon atoms, or aryl optionally substituted with a halogen atom.

39. A compound according to claim 1, wherein $R_L$ is of formula (X)

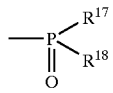
(X)

wherein R[17] and R[18], which may be identical or different, are each a halogen, or alkyl, cycloalkyl, alkoxy, aryloxy, aryl, aralkyloxy, perfluoroalkyl or aralkyl, in each case having up to 20 carbon atoms.

40. A process comprising polymerizing at least one monomer containing a carbon-carbon double bond which is capable of undergoing bulk, solution, emulsion or suspension free radical polymerization, at a temperature of 50° C. to 250° C., wherein polymerization is performed in the presence of a compound according to claim 38, as a polymerization initiator.

41. A process comprising polymerizing at least one monomer containing a carbon-carbon double bond which is capable of undergoing bulk, solution, emulsion or suspension free radical polymerization, at a temperature of 50° C. to 250° C., wherein polymerization is performed in the presence of a compound according to claim 40, as a polymerization initiator.

42. A process as claimed in claim 40, wherein the polymerized monomer(s) is (are) vinylaromatic monomers or optionally fluorinated acrylic monomers.

43. A process as claimed in claim 41, wherein the polymerized monomer(s) is (are) vinylaromatic monomers or optionally fluorinated acrylic monomers.

44. A process as claimed in claim 21, wherein the polymerized monomer(s) is (are) styrene, optionally fluorinated alkyl or aryl acrylate, optionally fluorinated alkyl or aryl methacrylate, an acrylamide or acrylonitrile.

45. A process according to claim 33, wherein said free-radical polymerization is performed at a temperature of 70° C. to 150° C.

46. A compound as claimed in claim 9, wherein R[6], R[7], and R[8] are each CH$_3$— and q, r, and s are each 2.

* * * * *

UNITED STATES PATENT AND TRADEMARK OFFICE
CERTIFICATE OF CORRECTION

PATENT NO. : 6,657,043 B1  Page 1 of 1
DATED : December 2, 2003
INVENTOR(S) : Guerret et al.

It is certified that error appears in the above-identified patent and that said Letters Patent is hereby corrected as shown below:

Column 34,
Line 13, delete "40" and insert -- 39 --.
Line 28, delete "9" and insert -- 19 --.

Signed and Sealed this

Eighteenth Day of May, 2004

JON W. DUDAS
*Acting Director of the United States Patent and Trademark Office*